(12) United States Patent
Liu

(10) Patent No.: US 11,826,534 B2
(45) Date of Patent: Nov. 28, 2023

(54) EAR, NOSE, AND THROAT IRRIGATOR

(71) Applicant: SHENZHEN ALEX TECHNOLOGY CO., LTD, Shenzhen (CN)

(72) Inventor: Qingquan Liu, Shenzhen (CN)

(73) Assignee: SHENZHEN ALEX TECHNOLOGY CO., LTD, Shenzhen (CN)

( * ) Notice: Subject to any disclaimer, the term of this patent is extended or adjusted under 35 U.S.C. 154(b) by 215 days.

(21) Appl. No.: 17/478,881

(22) Filed: Sep. 18, 2021

(65) Prior Publication Data

US 2023/0013619 A1 Jan. 19, 2023

(30) Foreign Application Priority Data

Jul. 13, 2021 (CN) .......................... 202121594878.4

(51) Int. Cl.
*A61M 11/00* (2006.01)
*A61M 3/02* (2006.01)

(52) U.S. Cl.
CPC ..... *A61M 3/0245* (2013.01); *A61M 2205/587* (2013.01); *A61M 2210/065* (2013.01); *A61M 2210/0618* (2013.01); *A61M 2210/0662* (2013.01)

(58) Field of Classification Search
CPC .......... A61M 11/00; A61M 2210/0618; A61M 2210/0681; A61M 2210/0662; A61M 3/0258; A61B 2017/246; A61C 17/032
See application file for complete search history.

(56) References Cited

U.S. PATENT DOCUMENTS

| | | | | |
|---|---|---|---|---|
| 5,176,654 A | * | 1/1993 | Schreiber | A61F 11/00 604/181 |
| 5,496,290 A | * | 3/1996 | Ackerman | A61M 3/0279 433/116 |
| 2007/0225662 A1 | * | 9/2007 | Rucinski | A61M 3/0262 604/290 |
| 2021/0023280 A1 | * | 1/2021 | Stanley | A61M 3/0262 |
| 2022/0168496 A1 | * | 6/2022 | Wagner | A61M 3/0258 |
| 2022/0203018 A1 | * | 6/2022 | Zhang | A61M 3/0283 |

* cited by examiner

*Primary Examiner* — Courtney B Fredrickson

(57) ABSTRACT

An ear, nose, and throat irrigator includes a bottle body, a housing; a water pump, a first tube body, a second tube body, and a shielding cover. A first end of the housing is connected with the bottle body. A spray head is arranged on a second end of the housing. The water pump is arranged in the housing. A first end of the first tube body is inserted into the bottle body. A second end of the first tube body is connected with a water inlet joint of the water pump. A first end of the second tube body is connected with a water outlet joint the water pump. A second end of the second tube body is connected with the spray head. The shielding cover is arranged on the spray head. The shielding cover is configured to shield water sprayed from the spray head.

16 Claims, 6 Drawing Sheets

EAR, NOSE, AND THROAT IRRIGATOR

TECHNICAL FIELD

The present disclosure relates to a field of ear, nose, and throat irrigators technology, and in particular to an ear, nose, and throat irrigator.

BACKGROUND

In various medical situations or daily life, it is often necessary to irrigate the ear, nose, and throat. For example, among the common diseases of otology, otitis media, middle ear effusion, and other clinical treatment operations need to clean up ear discharge. Clinicians perform further examination and treatment after cleaning an external auditory canal of a patient.

An ear, nose, and throat irrigator is a device configured to irrigate the ears, nose, and throat, and is used in various medical situations and daily life. However, during an irrigating process of the ear, nose, and throat irrigator, washing liquid is prone to splash around when sprayed onto a portion to be irrigated. Thus, the washing liquid splashes on a body of a user or the patient, or splashes on the ear, nose and throat irrigator, which is inconvenient to use.

SUMMARY

An object of the present disclosure is to provide an ear, nose, and throat irrigator, which is not easy to splash around and is convenient to use.

The present disclosure provides an ear, nose, and throat irrigator. The ear, nose, and throat irrigator comprises a bottle body, a housing, a water pump, a first tube body, a second tube body, and a shielding cover. A first end of the housing is connected with the bottle body. A spray head is arranged on a second end of the housing. The water pump is arranged in the housing. A first end of the first tube body is inserted into the bottle body. A second end of the first tube body is connected with a water inlet joint of the water pump. A first end of the second tube body is connected with a water outlet joint the water pump. A second end of the second tube body is connected with the spray head. The shielding cover is arranged on the spray head. The shielding cover is configured to shield water sprayed from the spray head.

Optionally, a surface of the spray head comprises a clamping protrusion. A through hole is on the shielding cover. A locking groove is arranged on a wall surface of the through hole. The shielding cover is sleeved on the spray head through the through hole. The clamping protrusion is engaged with the locking groove.

Optionally, anti-rotation protrusions are arranged on the surface of the spray head, and anti-rotation grooves are arranged on the wall surface of the through hole. The anti-rotation protrusions are embedded in the anti-rotation grooves.

Optionally, a resisting protrusion is arranged on the surface of the spray head. The resisting protrusion is arranged on one side of the spray head close to the housing. The resisting protrusion abuts against the shielding cover.

Optionally, the shielding cover is transparent.

Optionally, illuminating lights are arranged on an end surface of the housing close to the shielding cover.

Optionally, a thickness of the shielding cover gradually decreases from a middle portion to a periphery portion.

Optionally, the housing comprises a vertical portion and a horizontal portion. The vertical portion and the horizontal portion are connected in a "7" shape. The vertical portion is connected with the bottle body. The ear, nose, and throat irrigator further comprises a power supply. The power supply is arranged in the horizontal portion. The water pump is arranged in the vertical portion.

Optionally, the water pump is vertically arranged in the vertical portion; the water inlet joint faces the bottle body.

Optionally, the ear, nose, and throat irrigator further comprises a weight ball. The weight ball is connected to the first end of the first tube body inserted into the bottle body. A first channel and a second channel are defined in the weight ball. The first channel is communicated with the first tube body. The second channel is communicated with the first channel. A diameter of the second channel is greater than a diameter of the first channel.

In the ear, nose, and throat irrigator of the present disclosure, by arranging the shielding cover on the spray head, through shielding of the shielding cover, washing liquid is prevented from splashing around. Washing liquid is not easy to splash on a body of a user or a patient, and it is also not easy to splash on the ear, nose, and throat irrigator, which is convenient to use.

BRIEF DESCRIPTION OF DRAWINGS

The drawings are included to provide a further understanding of embodiments of the present disclosure, which form portions of the specification and are used to illustrate implementation manners of the present disclosure and are intended to illustrate operating principles of the present disclosure together with the description. Apparently, the drawings in the following description are merely some of the embodiments of the present disclosure, and those skilled in the art are able to obtain other drawings according to the drawings without contributing any inventive labor. In the drawing.

Figure 1:
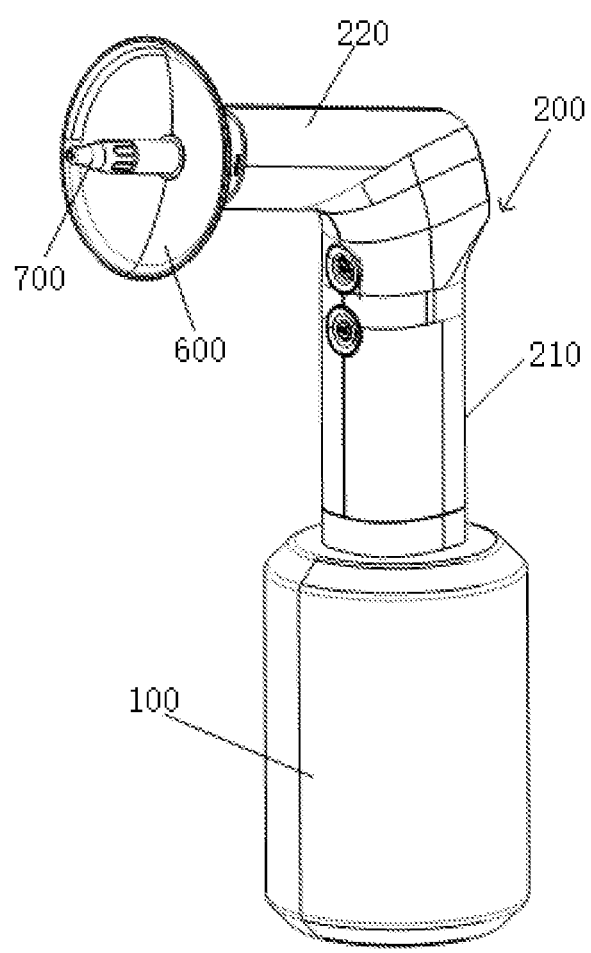
FIG. 1 is a schematic diagram of an ear, nose, and throat irrigator according to one embodiment of the present disclosure.

In the drawings:
100—bottle body; 200 housing; 210—vertical portion; 220—horizontal portion; 221—illuminating light; 300—water pump; 310—water inlet joint; 320—water outlet joint; 400—first tube body; 500—second tube body; 600—shielding cover; 610—through hole; 620—locking groove; 630—anti-rotation groove; 640—reinforcing protrusion; 700—spray head; 710—nozzle; 711—clamping block; 712—groove strip; 720—rod; 721—clamping protrusion; 722— anti-rotation protrusion; 723—resisting protrusion; 724—thread; 725—inserting tube; 800—counterweight ball; 810—first channel; 820—second channel; 900—power supply.

DETAILED DESCRIPTION

It should be understood that terms used herein and the specific structure and function details disclosed are only for describing specific embodiments and are representative. However, the present disclosure can be implemented in many alternative forms and should not be interpreted as limited to the embodiments described herein.

The present disclosure will be described in detail below with reference to the drawings and optional embodiments.

Figure 2:
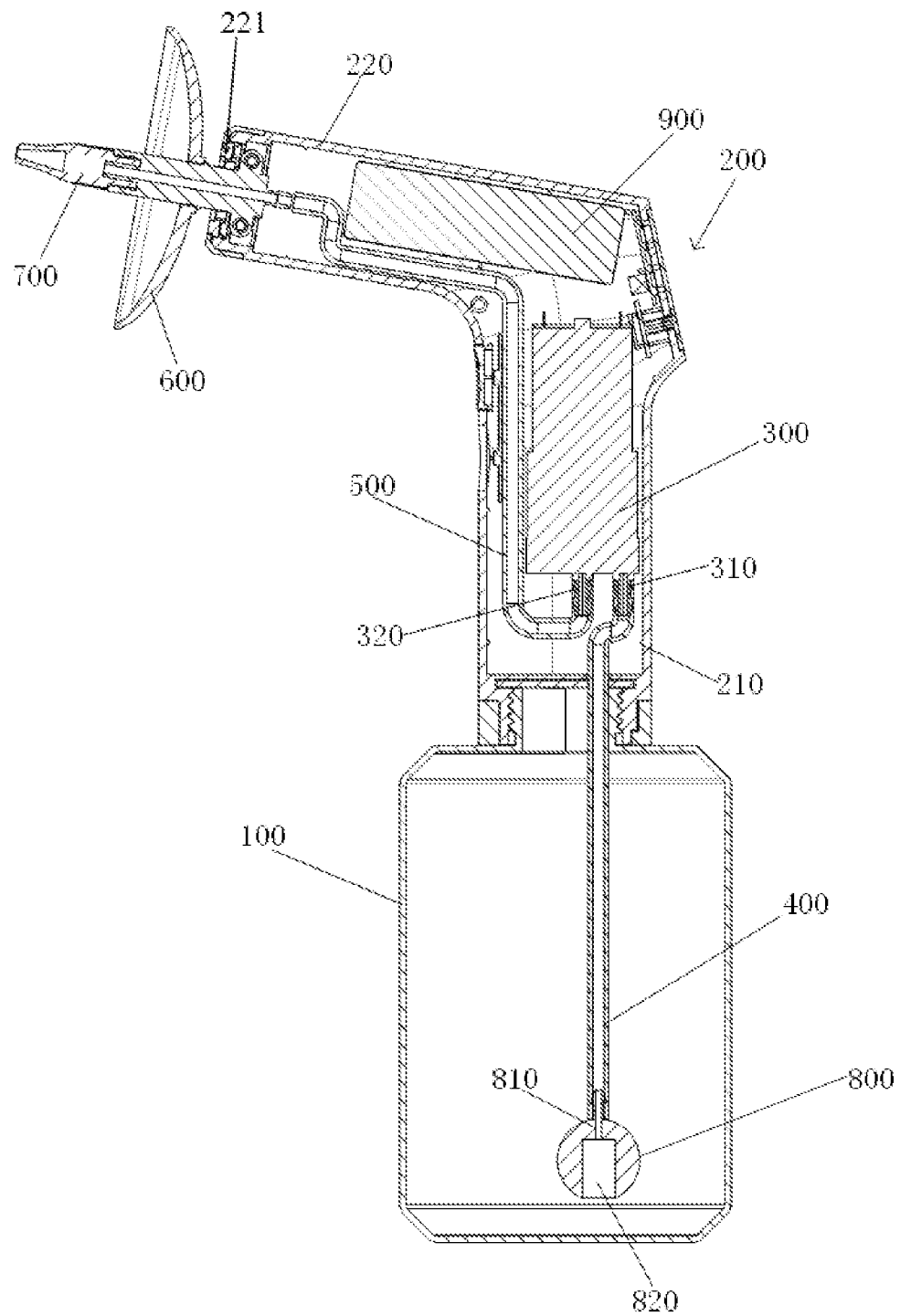
FIG. 2 is a cross-sectional view of an ear, nose, and throat irrigator according to one embodiment of the present disclosure.
Figure 3:
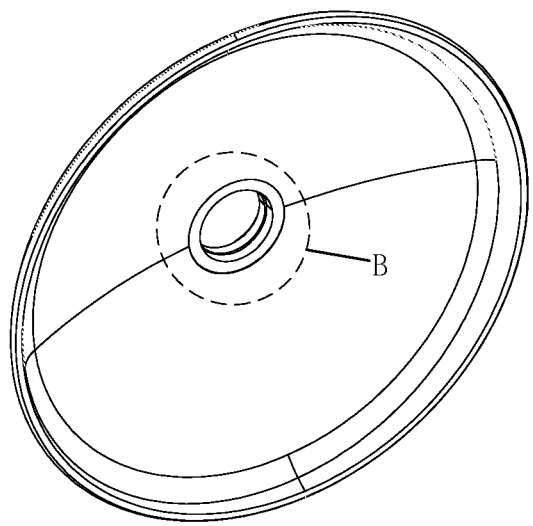
FIG. 3 is a schematic diagram of a shielding cover according to one embodiment of the present disclosure.
Figure 4:
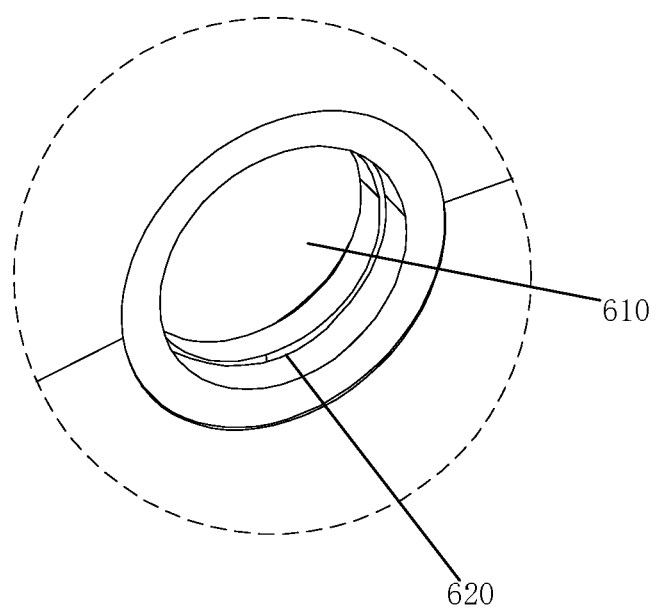
FIG. 4 is an enlarged view of portion B shown in FIG. 3.
Figure 5:
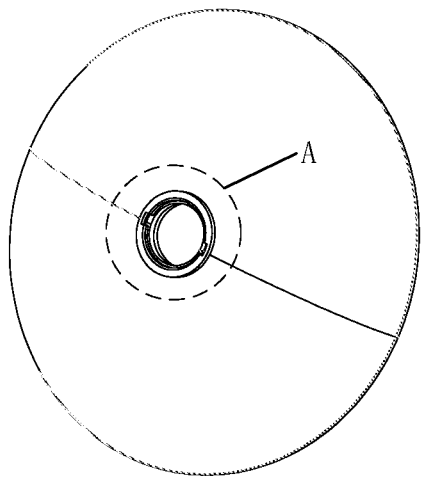
FIG. 5 is another schematic diagram of the shielding cover according to one embodiment of the present disclosure.
Figure 6:
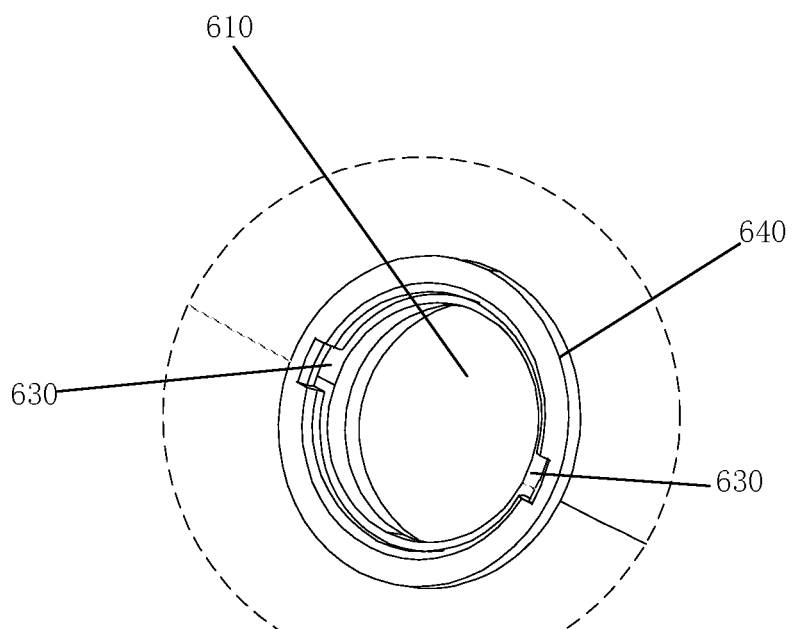
FIG. 6 is an enlarged view of portion A shown in FIG. 5.
Figure 7:
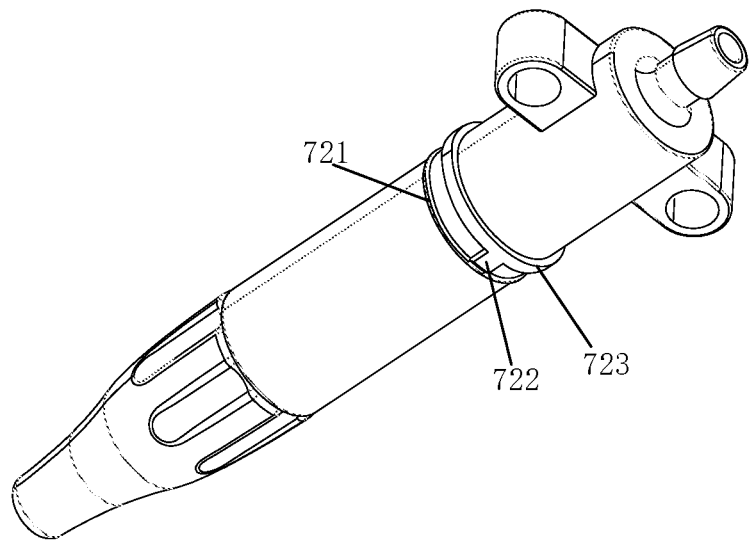
FIG. 7 is a schematic diagram of a spray head according to one embodiment of the present disclosure.
Figure 8:
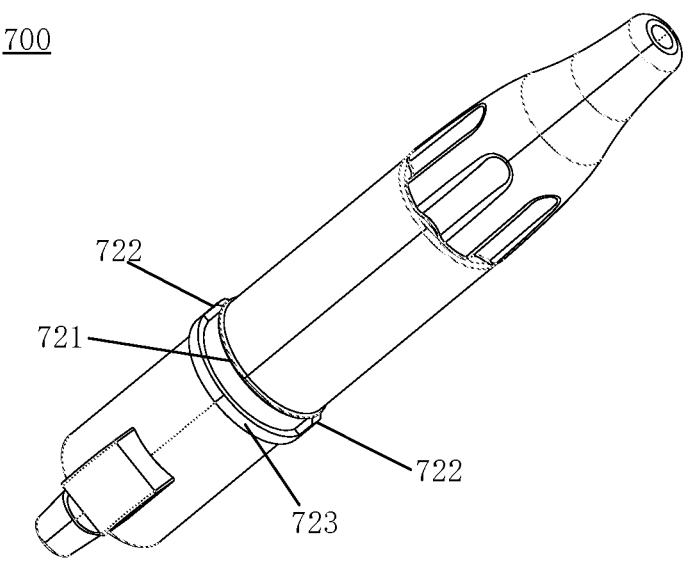
FIG. 8 is another schematic diagram of the spray head according to one embodiment of the present disclosure.

As shown in FIGS. 1 and 2, as one embodiment of the present disclosure, an ear, nose, and throat irrigator is disclosed. The ear, nose, and throat irrigator comprises a bottle body 100, a housing 200, a water pump 300, a first tube body 400, a second tube body 500, and a shielding cover 600. A first end of the housing 200 is connected with the bottle body 100. A spray head 700 is arranged on a second end of the housing 200. The water pump 300 is arranged in the housing 200. A first end of the first tube body 400 is inserted into the bottle body 100. A second end of the first tube body 400 is connected with a water inlet joint of the water pump 300. A first end of the second tube body 500 is connected with a water outlet joint the water pump 300. A second end of the second tube body 500 is connected with the spray head 700. The shielding cover 600 is arranged on the spray head 700. The shielding cover 600 is configured to shield water sprayed from the spray head 700.

During an irrigating process of a conventional ear, nose, and throat irrigator, washing liquid is prone to splash around when sprayed onto a portion to be irrigated. Thus, the washing liquid splashes on a body of a user or the patient, or splashes on the ear, nose and throat irrigator, which is inconvenient to use.

In the ear, nose, and throat irrigator of the present disclosure, by arranging the shielding cover 600 on the spray head 700, through shielding of the shielding cover 600, the washing liquid is prevented from splashing around. The washing liquid is not easy to splash on the body of the user or the patient, and it is also not easy to splash on the ear, nose, and throat irrigator, which is convenient to use.

An operation process of the ear, nose, and throat irrigator is described as follow. Specifically, the bottle body 100 is filled with washing liquid, and the washing liquid may be a therapeutic liquid or water. The bottle body 100 is connected with the housing 200, and the first tube body 400 is inserted into the bottle body 100 and inserted into the washing liquid. Then the water pump 300 is turned on, and the water pump 300 draws out the washing liquid through the first tube body 400 and pumps it to the spray head 700 through the second tube body 500. The washing liquid is sprayed from the spray head 700. When the washing liquid is sprayed on the portion to be irrigated, the washing liquid inevitably splashes around. At this time, the shielding cover 600 arranged on the spray head 700 blocks the splashing washing liquid, and the washing liquid is not easy to splash around.

Specifically, as shown in FIGS. 3-8, a surface of the spray head 700 comprises a clamping protrusion 721. A through hole 610 is on the shielding cover 600. A locking groove 620 is arranged on a wall surface of the through hole 610. The shielding cover 600 is sleeved on the spray head 700 through the through hole 610. The clamping protrusion 721 is engaged with the locking groove 620.

In the embodiment, through cooperation of the clamping protrusions 721 and the locking grooves 620, the shielding cover 600 is easily mounted on the spray head 700 and is easily detached from the spray head 700, so that the shielding cover 600 is conveniently detachable from the spray head 700. The shielding cover 600 is convenient to disassemble and assemble, and is convenient to replace. Specifically, the clamping protrusion 721 are arranged around a circumferential direction of the surface of the spray head 700, and the locking grooves 620 are arranged around one circle around a circumferential direction of the wall surface of the through hole 610, which makes fixing effect good, and the shielding cover 600 is not easy to fall off.

Specifically, at least one anti-rotation protrusion 722 is arranged on the surface of the spray head 700, and at least one anti-rotation groove 630 is arranged on the wall surface of the through hole 610. The at least one anti-rotation protrusion 722 is embedded in the at least one anti-rotation grooves 610.

In the embodiment, through cooperation of the at least one anti-rotation protrusions 722 and the at least one anti-rotation grooves 630, the shielding cover 600 is prevented from rotating relative to the spray head 700, and the fixing effect of the shielding cover 600 is good. Furthermore, in the embodiment, two anti-rotation protrusions 722 are provided, and two anti-rotation grooves 630 are provided accordingly. The two anti-rotation protrusions 722 are separately embedded in a respective anti-rotation grooves 630. Furthermore, the two anti-rotation protrusions 722 are arranged at an interval of 180°, the two anti-rotation grooves 630 are arranged corresponding to the two anti-rotation protrusions 722. The two anti-rotation protrusions 722 are arranged at the interval of 180°, so the force is more even, and the anti-rotation effect is good. In other embodiments, one, three, or even more anti-rotation protrusions 722 and one, three, or even more anti-rotation grooves 630 may be provided, which is not limited thereto. For example, when there are three anti-rotation protrusions 722 and three anti-rotation grooves 630, both of the three anti-rotation protrusions 722 and the anti-rotation grooves 630 are evenly spaced. A circumference angle formed between each two adjacent anti-rotation protrusions 722 is same. A circumference angle formed between each two adjacent anti-rotation grooves 630 is same.

Specifically, a resisting protrusion 723 is arranged on the surface of the spray head 700. The resisting protrusion 723 is arranged on one side of the spray head 600 close to the housing 200. The resisting protrusion 723 abuts against the shielding cover 600.

When the shielding cover 600 is in use, due to an impact of the washing liquid, the shielding cover 600 may gradually move axially toward the housing 200. In the embodiment, by providing the resisting protrusion 723 on the spray head 700 on the side that the shielding cover 600 is close to the housing 200, the shielding cover 600 is prevented from moving axially along the spray head 700 and approaching the housing 200 by resistance of the resisting protrusions 723. Furthermore, the resisting protrusion 723 is arranged around a circumferential direction of the surface of the spray head 700, and the resisting effect is good. In other embodiments, multiple resisting protrusions 723 may be provided and the resisting protrusions 723 are arranged at intervals.

Specifically, a reinforcing protrusion 640 is arranged on an edge of a side of the through hole 610 facing the housing 200. The reinforcing protrusion 640 is arranged around a periphery of an edge of the through hole 610. The through hole 610 is a position where the force is relatively large and frequently, and because the through hole 610 is defined, a structural strength of the through hole 610 is small. In the embodiment, by providing the reinforcing protrusion 640, a structural strength of a periphery of the through hole 610 is strengthened, and the shielding cover 600 is prevented from being damaged.

Specifically, the shielding cover 600 is transparent. In the embodiment, the shielding cover 600 is set to be transparent, and the shielding cover 600 does not obstruct the user's sight while shielding splashing of the washing liquid, which is convenient for the user to observe a washing portion. Furthermore, the shielding cover 600 is make of a soft, deformable material, such as rubber, silicone, and the like. The soft shielding cover 600 is easy to deform so it is easy to install. Furthermore, a thickness of the shielding cover 600 gradually decreases from a middle portion to a periphery portion. A structure of the washing portion of the ear, nose and throat is relatively complicated, and it is difficult to observe. In the embodiment, the thickness of the shielding cover 600 gradually decreases from the middle portion to the periphery portion, so a shape of the shielding cover 600 is thick in the middle portion and thin at the periphery portion, so that the shielding cover 600 has a magnifying function, similar to a magnifying glass. In this way, the shielding cover 600 magnifies the washing portion, which is convenient for the user to observe the washing portion.

Specifically, a surface of the shielding cover 600 facing away from the housing 200 is curved, and the curved surface is recessed toward the housing 200. The surface of the shielding cover 600 facing away from the housing 200 is used to shield the splashed washing liquid. By arranging the surface as the curved surface and recessed toward the housing 200, the splashed washing liquid is buffer and received, which prevent the washing liquid from splashing back to the washing portion. At the same time, the curved surface also plays a role of gathering the splashing washing liquid to prevent the washing liquid from splashing again.

Specifically, illuminating lights 221 are arranged on an end surface of the housing 200 close to the shielding cover 600. The structure of the washing portion of the ear, nose, and throat is relatively complicated, light is poor, and it is difficult to observe. In the embodiment, the washing portion is illuminated by the illuminating light 221, which is convenient for the user to observe the washing portion. Furthermore, there are four illuminating lamps 221, and the four illuminating lights are evenly arranged on the end surface of the housing 200 close to the shielding cover 600, so that the light is stronger and a brightness is uniform.

As shown in FIG. 2, the housing 200 comprises a vertical portion 210 and a horizontal portion 220. The vertical portion 210 and the horizontal portion 220 are connected in a "7" shape. The vertical portion 210 is connected with the bottle body 100. The ear, nose, and throat irrigator further comprises a power supply 900. The power supply 900 is arranged in the horizontal portion 220. The water pump 300 is arranged in the vertical portion 210.

The housing 200 is in the shape of "7", and the spray head 700 is arranged on the end surface of the horizontal portion 220 to facilitate washing by the user. More importantly, a weight of the water pump 300 is relatively large, to arrange the water pump 300 in the vertical portion 210 is able to lower a center of gravity of the ear, nose, and throat irrigator. The weight is reasonable, so the ear, nose, and throat irrigator is placed stably. When the user picks it up, it is also labor-saving. At the same time, arranging the power supply 900 in the horizontal portion 220 is able to fully and rationally utilize and internal space of the housing 200.

Specifically, the water pump 300 is vertically arranged in the vertical portion 210. The water inlet joint 310 faces the bottle body 100. In the embodiment, the water pump 300 is arranged vertically and the water inlet joint 310 faces the bottle body 100. In this way, water inlet of the first pipe body 400 does not need to bend, and the water inlet is smooth.

Specifically, the ear, nose, and throat irrigator further comprises a weight ball 800. The weight ball 800 is connected to the first end of the first tube body 400 inserted into the bottle body 100. A first channel 810 and a second channel 820 are defined in the weight ball 800. The first channel 810 is communicated with the first tube body 400. The second channel 820 is communicated with the first channel 810. A diameter of the second channel 820 is greater than a diameter of the first channel 810.

The weight ball 800 has a certain weight and straightens the first tube body 400 to facilitate smooth water inlet. The weight ball 800 comprises the first channel 810 and the second channel 820. The second channel 820 has a larger diameter than the first channel 810, which reduces water inlet resistance, facilitates the washing liquid to quickly enter the first tube body 400, and reduces a working load of the water pump 300.

Figure 9:
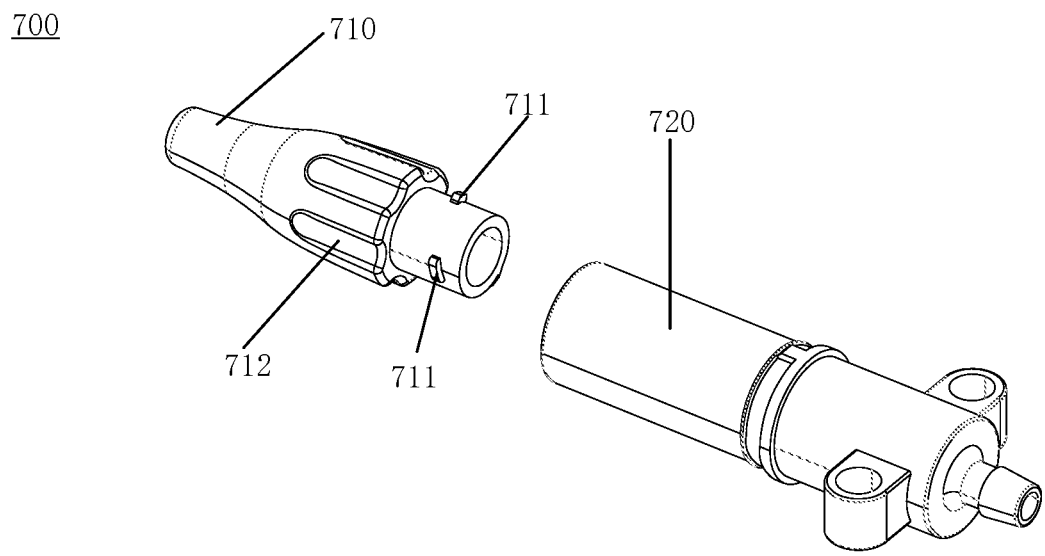
FIG. 9 is an exploded schematic diagram of the spray head according to one embodiment of the present disclosure.
Figure 10:
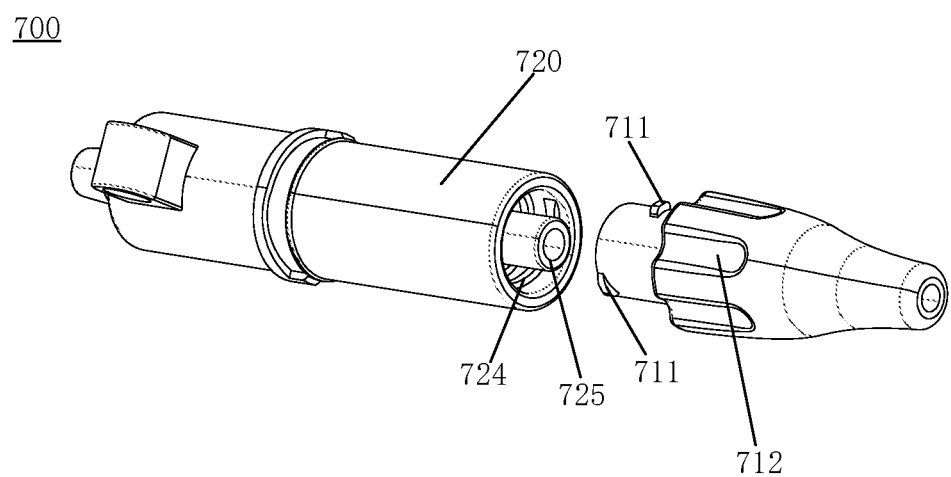
FIG. 10 is another exploded schematic diagram of the spray head according to one embodiment of the present disclosure.

Specifically, as shown in FIGS. 9 and 10, the spray head 700 comprises a nozzle 710 and a rod 720. The rod 720 is connected with the housing 200 and connected with the second tube body 500. A clamping block 711 is arranged on one end of the nozzle 710. Threads 724 are arranged on an inner wall of the rod 720, and the clamping block 711 is inserted into the rod and engaged with the threads 724. The nozzle 710 is screwed to the rod 720 through cooperation of the clamping block 711 and the threads 724, and the nozzle 710 is replaceable. Furthermore, a inserting tube 725 is arranged in the rod 720. When the nozzle 710 is screwed on the rod 720, the inserting tube 725 is inserted into the nozzle 710, which make connection strong. Furthermore, groove strips 712 are arranged on a surface of the nozzle 710 to increase friction of the nozzle 710, so when the user rotates the nozzle 710, it is not easy to slip, which saves effort.

The above content is a further detailed description of the present disclosure in combination with specific optional embodiments, and it is not considered that the specific implementation of the present disclosure is limited to these descriptions. For those of ordinary skill in the field to which the present disclosure belongs, a number of simple deductions or substitutions can be made without departing from the concept of the present disclosure, which should be regarded as falling within the protection scope of the present disclosure.

What is claimed is:

1. An ear, nose, and throat irrigator, comprising: a bottle body, a housing, a water pump, a first tube body, a second tube body, and a shielding cover; wherein a first end of the housing is connected with the bottle body; a spray head is arranged on a second end of the housing; the water pump is arranged in the housing; a first end of the first tube body is inserted into the bottle body; a second end of the first tube body is connected with a water inlet joint of the water pump; a first end of the second tube body is connected with a water outlet joint of the water pump; a second end of the second tube body is connected with the spray head; the shielding cover is arranged on the spray head; the shielding cover is configured to shield water sprayed from the spray head, wherein the shielding cover is transparent, wherein illuminating lights are arranged on an end surface of the housing adjacent to the shielding cover, the illuminating lights are configured for illuminating a washing portion for users to observe, wherein a surface of the spray head comprises a clamping protrusion; a through hole is on the shielding cover; a locking groove is arranged on a wall surface of the through hole; the shielding cover is sleeved on the spray head through the through hole; the clamping protrusion is engaged with the locking groove; and wherein anti-rotation protrusions are arranged on the surface of the spray head, and anti-rotation grooves are arranged on the wall surface of the through hole; the anti-rotation protrusions are embedded in the anti-rotation grooves.

2. The ear, nose, and throat irrigator according to claim 1, wherein a resisting protrusion is arranged on the surface of the spray head; the resisting protrusion is arranged on one side of the spray head close to the housing; the resisting protrusion abuts against the shielding cover.

3. The ear, nose, and throat irrigator according to claim 2, wherein the ear, nose, and throat irrigator further comprises a weight ball; the weight ball is connected to the first end of the first tube body inserted into the bottle body; a first channel and a second channel are defined in the weight ball; the first channel is communicated with the first tube body; the second channel is communicated with the first channel; a diameter of the second channel is greater than a diameter of the first channel.

4. The ear, nose, and throat irrigator according to claim 1, wherein a thickness of the shielding cover gradually decreases from a middle portion to a periphery portion.

5. The ear, nose, and throat irrigator according to claim 1, wherein the housing comprises a vertical portion and a horizontal portion; the vertical portion and the horizontal portion are connected in a "7" shape; the vertical portion is connected with the bottle body; the ear, nose, and throat irrigator further comprises a power supply; the power supply is arranged in the horizontal portion; the water pump is arranged in the vertical portion.

6. The ear, nose, and throat irrigator according to claim 5, wherein the water pump is vertically arranged in the vertical portion; the water inlet joint faces the bottle body.

7. The ear, nose, and throat irrigator according to claim 1, wherein the ear, nose, and throat irrigator further comprises a weight ball; the weight ball is connected to the first end of the first tube body inserted into the bottle body; a first channel and a second channel are defined in the weight ball; the first channel is communicated with the first tube body; the second channel is communicated with the first channel; a diameter of the second channel is greater than a diameter of the first channel.

8. An ear, nose, and throat irrigator, comprising: a bottle body, a housing, a water pump, a first tube body, a second tube body, and a shielding cover; wherein a first end of the housing is connected with the bottle body; a spray head is arranged on a second end of the housing; the water pump is arranged in the housing; a first end of the first tube body is inserted into the bottle body; a second end of the first tube body is connected with a water inlet joint of the water pump; a first end of the second tube body is connected with a water outlet joint of the water pump; a second end of the second tube body is connected with the spray head; the shielding cover is arranged on the spray head; the shielding cover is configured to shield water sprayed from the spray head, wherein a surface of the spray head comprises a clamping protrusion; a through hole is on the shielding cover; a locking groove is arranged on a wall surface of the through hole; the shielding cover is sleeved on the spray head through the through hole; the clamping protrusion is engaged with the locking groove, wherein anti-rotation protrusions are arranged on the surface of the spray head, and anti-rotation grooves are arranged on the wall surface of the through hole; the anti-rotation protrusions are embedded in the anti-rotation grooves.

9. The ear, nose, and throat irrigator according to claim 8, wherein a resisting protrusion is arranged on the surface of the spray head; the resisting protrusion is arranged on one side of the spray head close to the housing; the resisting protrusion abuts against the shielding cover.

10. The ear, nose, and throat irrigator according to claim 9, wherein a thickness of the shielding cover gradually decreases from a middle portion to a periphery portion.

11. The ear, nose, and throat irrigator according to claim 8, wherein the housing comprises a vertical portion and a horizontal portion; the vertical portion and the horizontal portion are connected in a "7" shape; the vertical portion is connected with the bottle body; the ear, nose, and throat irrigator further comprises a power supply; the power supply is arranged in the horizontal portion; the water pump is arranged in the vertical portion.

12. The ear, nose, and throat irrigator according to claim 11, wherein the water pump is vertically arranged in the vertical portion; the water inlet joint faces the bottle body.

13. The ear, nose, and throat irrigator according to claim 8, wherein the ear, nose, and throat irrigator further comprises a weight ball; the weight ball is connected to the first end of the first tube body inserted into the bottle body; a first channel and a second channel are defined in the weight ball; the first channel is communicated with the first tube body; the second channel is communicated with the first channel; a diameter of the second channel is greater than a diameter of the first channel.

14. An ear, nose, and throat irrigator, comprising: a bottle body, a housing, a water pump, a first tube body, a second tube body, and a shielding cover; wherein a first end of the housing is connected with the bottle body; a spray head is arranged on a second end of the housing; the water pump is arranged in the housing; a first end of the first tube body is inserted into the bottle body; a second end of the first tube body is connected with a water inlet joint of the water pump; a first end of the second tube body is connected with a water outlet joint of the water pump; a second end of the second tube body is connected with the spray head; the shielding cover is arranged on the spray head; the shielding cover is configured to shield water sprayed from the spray head, wherein the housing comprises a vertical portion and a horizontal portion; the vertical portion and the horizontal portion are connected in a "7" shape; the vertical portion is connected with the bottle body; the ear, nose, and throat irrigator further comprises a power supply; the power supply is arranged in the horizontal portion; the water pump is arranged in the vertical portion.

15. The ear, nose, and throat irrigator according to claim 14, wherein the water pump is vertically arranged in the vertical portion; the water inlet joint faces the bottle body.

16. The ear, nose, and throat irrigator according to claim 14, wherein the ear, nose, and throat irrigator further comprises a weight ball; the weight ball is connected to the first end of the first tube body inserted into the bottle body; a first channel and a second channel are defined in the weight ball; the first channel is communicated with the first tube body; the second channel is communicated with the first channel; a diameter of the second channel is greater than a diameter of the first channel.

* * * * *